(12) United States Patent
Chen et al.

(10) Patent No.: US 6,570,014 B1
(45) Date of Patent: May 27, 2003

(54) PROCESS FOR PREPARING TRIAZOLOPYRIMIDINE DERIVATIVES

(75) Inventors: Chien-Hsing Chen, Taichung (TW); Chun-Lin Yeh, Taichung (TW); Yu-Hwa Chuang, Taichung (TW)

(73) Assignee: Sinon Corporation, Taichung (TW)

( * ) Notice: Subject to any disclaimer, the term of this patent is extended or adjusted under 35 U.S.C. 154(b) by 0 days.

(21) Appl. No.: 10/134,504

(22) Filed: Apr. 30, 2002

(51) Int. Cl.⁷ ............................................. C07D 487/04
(52) U.S. Cl. ....................................... 544/263
(58) Field of Search .......................... 544/263

(56) References Cited

U.S. PATENT DOCUMENTS 3,689,488 A * 9/1972 Dukes ........................ 544/263

* cited by examiner

*Primary Examiner*—John M. Ford
(74) *Attorney, Agent, or Firm*—Bacon & Thomas

(57) ABSTRACT

A process for preparing triazolopyrimidine derivatives of the formula (I):

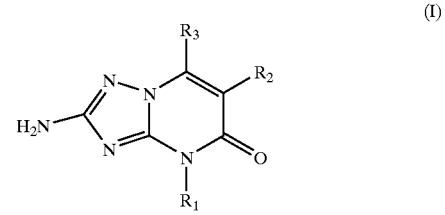

wherein $R_1$ represents a hydrogen or an alkyl radical of one to ten carbon atoms, or a cycloalkyl radical of three to six carbon atoms, or an alkenyl radical of up to four carbon atoms; $R_2$ represents a hydrogen, a halogen atom, a hydroxyalkyl or alkyl radical of one to ten carbon atoms; $R_3$ represents a hydrogen, a hydroxyalkyl or alkyl radical of one to four carbon atoms; by rapidly preparing diamino-1,2,4-triazole which is reacted with an aldehyde to form an imide which is reacted with an α,β-unsaturated acid derivative, the reaction product of which is hydrolyzed in the presence of an acid to produce the triazolopyrimidine derivatives of formula (I). The compounds of the formula (I) are capable of preventing bronchospasm.

26 Claims, No Drawings

PROCESS FOR PREPARING TRIAZOLOPYRIMIDINE DERIVATIVES

FIELD OF THE INVENTION

This invention relates to a novel process for preparing triazolopyrimidine derivatives of the formula (I):

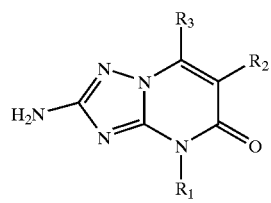

wherein $R_1$ represents a hydrogen or an alkyl radical of one to ten carbon atoms, or a cycloalkyl radical of three to six carbon atoms, or an alkenyl radical of up to four carbon atoms; $R_2$ represents a hydrogen, a halogen atoms, a hydroxyalkyl or alkyl radical of one to ten carbon atoms; $R_3$ represents a hydrogen, a hydroxyalkyl or alkyl radical of one to four carbon atoms.

BACKGROUND OF THE INVENTION

The compounds of the formula (I) are known and described in U.S. Pat. No. 3,689,488. They are capable of preventing bronchospasm and therefore useful in the treatment of diseases that involve spasm or constriction of the bronchial muscle, for example asthma or bronchitis. A process for the preparation of the formula (I) described in U.S. Pat. No. 3,689,488 are summarized as follows:

(a) Preparation of diamino-1,2,4-triazole (shown in Scheme 1)

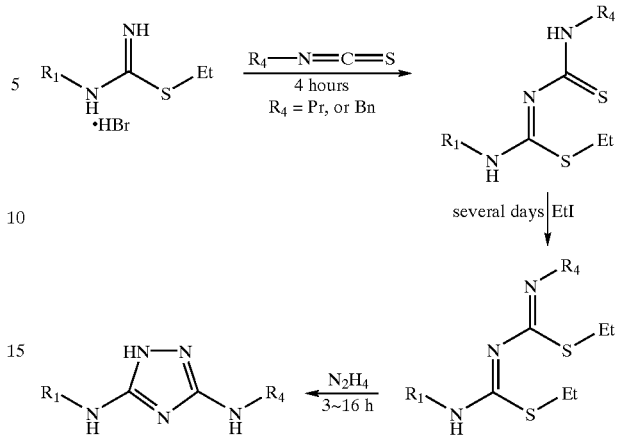

(b) Preparation of triazolopyrimidines (shown in Scheme 2)

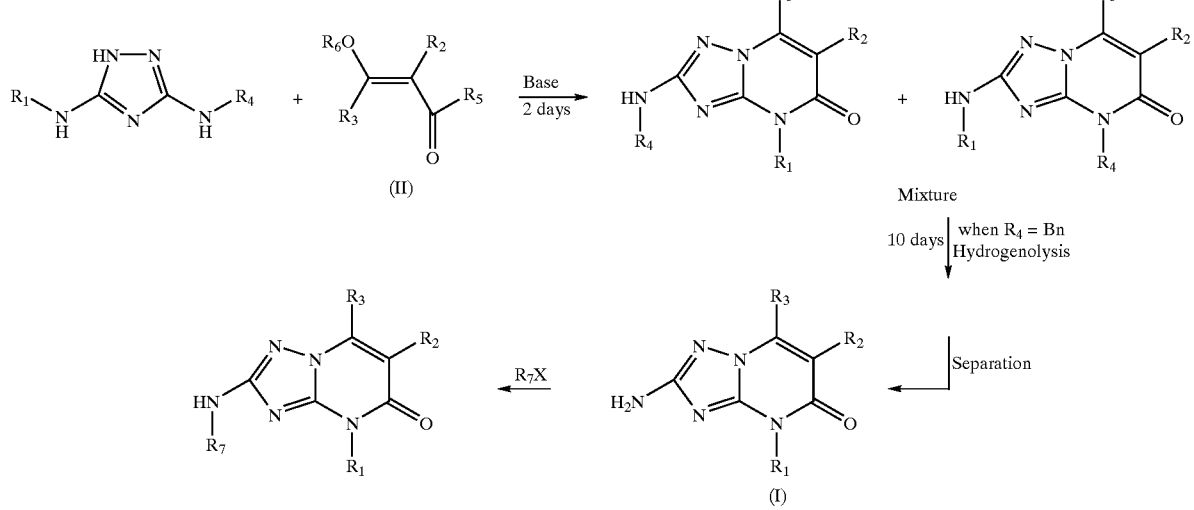

There are several disadvantages for manufacturing in the aforementioned processes. First of all, the process for preparing diamino-1,2,4-triazole (Scheme 1) taking several days is inefficient. Second, the condensation of diamino-1,2,4-triazole and α, β-unsaturated acid derivatives of the formula (II) that obtained mixture isomers is unselective and need further purification (Scheme 2). Third, The hydrogenolysis of benzyl group (deprotection of amino group) to get triazolopyrimidines of the formula (I) taking 10 days is time-consuming (Scheme 2). From the commercial point of view, the processes shown in scheme 1 and 2 are inefficient and costly.

SUMMARY OF THE INVENTION

Therefore, it is an object of the present invention to provide a more efficient, cheaper and selective process for preparing triazolopyrimidines derivatives of formula (I) that is capable of overcoming the aforesaid drawbacks.

According to the present invention, there is provided a process for preparing triazolopyrimidines derivatives of the formula (I). This process comprises preparing rapidly diamino-1,2,4-triazole of the formula (III) from dialkyl cyanodithioimino carbonate of the formula (V); and efficient protection and deprotection of amino group; and selective condensation of α, β-unsaturated acid derivatives of the formula (II) and imine of the formula (VI).

DETAILED DESCRIPTION OF THE INVENTION

A process for preparing triazolopyrimidines derivatives of the formula (I) according to the present invention comprises four steps. The first step is the efficient preparation of diamino-1,2,4-triazole of the formula (III), wherein 1 to 2 equivalent of alkyl amine of the formula (IV) is added slowly into the mixture of the dialkyl cyanodithioimino carbonate of the formula (V) (1 equivalent) and appropriate solvent at room temperature, and then 1 to 4 equivalent of the hydrazine is added dropwisely after heating to reflux.

Scheme 3

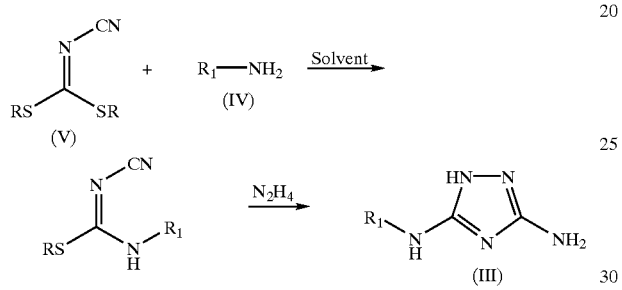

Schematic illustration of preparing diamino-1,2,4-triazole of the formula (III) is shown in scheme 3, wherein $R_1$ has the meaning indicated above; and R represents an alkyl radical of one to four carbon atoms; and solvent can use water, acetonitrile or alcoholic solvent, such as methanol, ethanol, propanol, or butanol, etc.

The second step is the formation of imine of the formula (VI), wherein 1 to 5 equivalent of aldehyde of the formula (VII) is reacted with 1 equivalent of the diamino-1,2,4-triazole of the formula (III) in an organic solvent under acid catalysis (0 to 1 equivalent) at 50~150° C.

Scheme 4

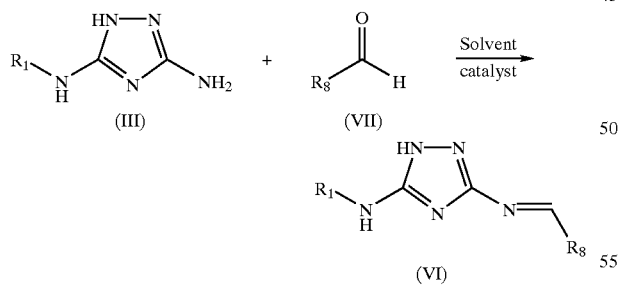

Schematic illustration of preparing imine of the formula (VI) is shown in scheme 4, wherein $R_1$ has the meaning indicated above; and $R_8$ represents an alkyl radical of one to ten carbon atoms, or a phenyl, or a substituted phenyl; and solvent can use acetonitrile, toluene; xylene, chlorobenzene, chloroform, dichloromethane, ethylene dichloride or alcoholic solvent, such as methanol, ethanol, propanol, or butanol, etc.; and catalyst can be not necessary to add, or catalyst can be organic or inorganic acid such as acetic acid, toluene sulfonic acid, sulfuric acid, or hydrogen chloride.

The third step is the condensation of α, β-unsaturated acid derivatives of the formula (II) and imine of the formula (VI), wherein 1 to 2 equivalent of α, β-unsaturated acid derivatives of the formula (II) is reacted with 1 equivalent of the imine of the formula (VI) in the present of a base (0.1 to 2 equivalent) and a polymer inhibitor (0.005 to 0.2 equivalent) in an organic solvent at reflux temperature (40~150° C.)

Scheme 5

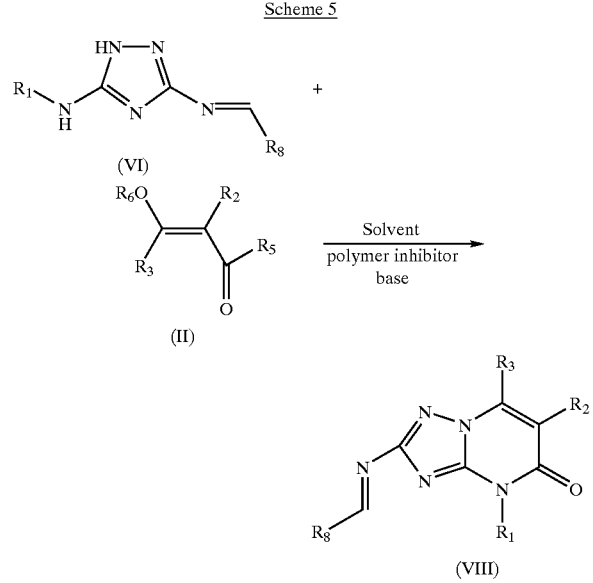

Schematic illustration of the condensation of α, β-unsaturated acid derivatives of the formula (II) and imine of the formula (VI) is shown in scheme 5, wherein $R_1$, $R_2$, $R_3$ and $R_8$ have the meaning indicated above, and $R_5$ represents a halogen atom or $OR_9$, wherein $R_9$ represents an alkyl radical of one to six carbon atoms; and $R_6$ represents an alkyl radical of one to six carbon atoms; and the solvent can be acetonitrile, toluene, xylene, chlorobenzene, chloroform, dichloromethane or ethylene dichloride; and the base can be metal carbonate or metal hydrogencarbonate, wherein metal can be Li, Na, K, Rb, Cs, Be, Mg, Ca, Sr, or Ba etc.; and polymer inhibitor can use hydroquinone or monomethyl ether hydroquinone.

The last step is the formation of triazolopyrimidines derivatives of the formula (I), wherein imine of the formula (VIII) is hydrolyzed in the present of an acid (0.1 to 10 equivalent), water and solvent at room temperature to refluxing temperature.

Scheme 6

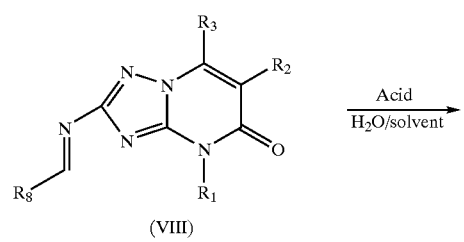

-continued

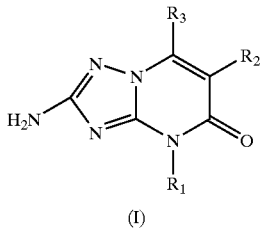

Schematic illustration of the formation of triazolopyrimidines derivatives of the formula (I) is shown in scheme 6, wherein $R_1$, $R_2$, $R_3$ and $R_8$ have the meaning indicated above; and the acid can be inorganic or organic acid such as hydrochloride, sulfuric acid, acetic acid, or oxalic acid, etc.; and solvent can use water, methanol, ethanol, acetonitrile, toluene, xylene, chlorobenzene, chloroform, dichloromethane, or ethylene dichloride, etc.

The following non-limitative examples further illustrate the present invention.

EXAMPLE 1

Preparation of $N^5$-Propyl-1H-[1,2,4]triazole-3,5-diamine

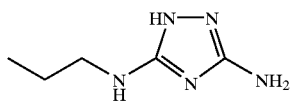

1200 g (8.13 mole) of dimethyl cyanodithioimino carbonate was dissolved in 6 Kg of isopropanol in a 10-liter, four-necked flask equipped with a reflux condenser, thermometer, addition funnel, and mechanical stirrer. 538 g (8.94 mole) of n-propyl amine was added dropwisely over a period of 2 hours at room temperature. After the reaction mixture was stirred for another 20 minutes, the temperature was raised to refluxing temperature and then 1224 g (20.8 mole) of hydrazine monohydrate (85%) was added slowly, followed by reflux for 2~3 hours. Then 80% of isopropanol was distilled out under reduced pressure. The residue was cooled to 5~10° C. After filtering and drying, the white solid of $N^5$-Propyl-1H-[1,2,4]triazole-3,5-diamine was obtained. The yield is 1075 g (AI 98%, 92% of the theoretical amount). The melting point is 148~149° C.

EXAMPLE 2

Preparation of $N^3$-Benzylidene-$N^5$-propyl-1H-[1,2,4]triazole-3,5-diamine

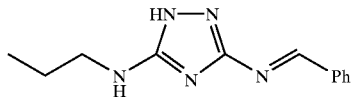

Method 1

A 5-7liter flask equipped with a reflux condenser, thermometer, and mechanical stirrer was charged with 251.8 g (1.75 mole) of $N^5$-Propyl-1H-[1,2,4]triazole-3,5-diamine, 1.24 liter of methanol, 194.8 g (1.84 mole) of benzaldehyde and then heated to reflux for 6~10 hours. After checking the end of the reaction by LC (peak area of $N^5$-Propyl-1H-[1,2,4]triazole-3,5-diamine is less than 1%), ⅔ volume of the solvent was distilled out from the mixture under reduced pressure. The residue was cooled to room temperature and the yellow solid of $N^3$-Benzylidene-$N^5$-propyl-1H-[1,2,4]triazole-3,5-diamine was precipitated. Collecting the precipitate by filtration, 381~389 g (purity is 98%, 93~95% of the theoretical amount) of the desired product was obtained after drying.

Similar results were achieved when. methanol was replaced by ethanol, toluene or acetonitrile. When 5.2 g (0.087 mole) of acetic acid was used in these cases or/and water was removed azeotropically, the reaction time could be shortened to 1~4 hours without obvious changing the yield and purity.

Method 2

A 5-liter flask equipped with a reflux condenser, thermometer, and mechanical stirrer was charged with 251.8 g (1.75 mole) of $N^5$-Propyl-1H-[1,2,4]triazole-3,5-diamine, 1.75 liter of toluene, 203.4 g (1.92 mole) of benzaldehyde and 5.2 g (0.087 mole) of acetic acid and then heated to reflux for 1~3 hours. During the reaction, water was formed as by-product and removed azeotropically. After checking the end of the reaction by LC (peak area of $N^5$-Propyl-1H-[1,2,4]triazole-3,5-diamine is less than 1%), the mixture was cooled down and gave the crude $N^3$-Benzylidene-$N^5$-propyl-1H-[1,2,4]triazole-3,5-diamine suspension solution, which was used for the next stage without purification.

EXAMPLE 3

Preparation of 2-(Benzylidene-amino)-6-methyl-4-propyl-4H-[1,2,4]triazolo[1,5-a]pyrimidin-5-one

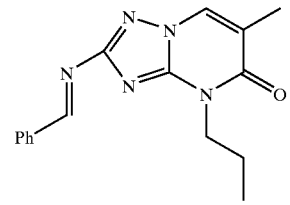

Method 1

A 5-liter flask equipped with a reflux condenser, thermometer, and mechanical stirrer was charged with 401.03 g (1.75 mole) of $N^3$-Benzylidene-$N^5$-propyl-1H-[1,2,4]triazole-3,5-diamine, 253 g (1.83 mole) of potassium carbonate, 250 g (1.92 mole) of methyl 2-methoxy-aphamethyl acrylate, 1.1 g (0.009 mole) of p-methoxy phenol, and 1750 ml of acetonitrile and then heated to reflux for 24~28 hours. After distilling out acetonitrile under reduced pressure, water was added and the mixture was extracted with ethylene dichloride. Ethylene dichloride was removed from extract and then 406~432 g (77~82% of the theoretical amount) of the desired product was obtained after drying.

Similar result was achieved when acetonitrile was replaced by toluene.

Method 2

253 g (1.83 mole) of potassium carbonate, 250 g (1.92 mole) of methyl 2-methoxy-apha-methyl acrylate, and 1.1 g (0.009 mole) of p-methoxy phenol were added to the $N^3$-Benzylidene-$N^5$-propyl-1H-[1,2,4]triazole-3,5-diamine suspension solution prepared in example 2 (Method 2). After refluxing for 12~20 hours, the mixture was cooled to room temperature and then 1 liter of water was added. The solid of 2-(Benzylidene-amino)-6-methyl-4-propyl-4H-[1,2,4]triazolo[1,5-a]-pyrimidin-5-one was collected by filtration and the filtrate was separated into two layers which organic layer could be reused for example 2. The crude 2-(Benzylidene-amino)-6-methyl-4-propyl-4H-[1,2,4] triazolo[1,5-a]-pyrimidin-5-one was used for the next stage without purification.

EXAMPLE 4

Preparation of 2-Amino-6-methyl-4-propyl-4H-[1,2,4]triazolo[1,5-a]pyrimidin-5-one

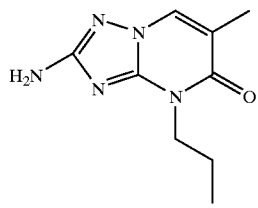

1750 ml of 2N HCl (3.5 mole) was added to the crude 2-(benzylidene-amino)-6-methyl-4-propyl-4H-[1,2,4]triazo [1,5-a]-pyrimidin-5-one prepared in example 3 (Method 2). The mixture was heated to 65~70° C. for 30 minutes and the hydrolyzed benzaldehyde was removed azeotropically under reduced pressure. After benzaldehyde was removed completely, the mixture was cooled down and the pH value was adjusted to 7~8 with 45% of $NaOH_{(aq)}$. Then the resulted suspension was filtered and the light yellow solid of 2-amino-6-methyl-4-propyl-4H-[1,2,4]triazolo[1,5-a] pyrimidin-5-one (purity is 98%) was obtained after drying. The yield is 264~275 g (73~76% of the theoretical amount from example 2).

Similar result was achieved when additional 1500 ml of methanol was used as solvent and hydrolyzed at room temperature.

What is claimed is:

1. A process for preparation of triazolopyrimidine derivatives of the formula (I)

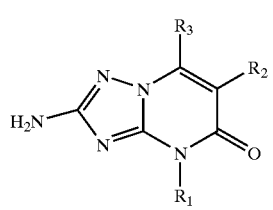

(I)

wherein
$R_1$ represents a hydrogen or an alkyl radical of one to ten carbon atoms or a cycloalkyl radical of three to six carbon atoms, or an alkenyl radical of up to four carbon atoms;
$R_2$ represents a hydrogen, a halogen atoms, a hydroxyalkyl or alkyl radical of one to ten carbon atoms;
$R_3$ represents a hydrogen, a hydroxyalkyl or alkyl radical of one to four carbon atoms;
comprises the steps of
(a) reacting dialkyl cyanodithioimino carbonate of the formula (V), wherein R represents an alkyl radical of one to four carbon atoms, with alkyl amine of formula (IV), wherein $R_1$ has the meaning as indicated above, in the present of an appropriate solvent at room temperature, and then add hydrazine dropwisely after heating to reflux, to give a compound of diamino-1,2,4-triazole of the formula (III), wherein $R_1$ has the meaning as indicated above;

(b) reacting the compound of the formula (III), wherein $R_1$ has the meaning as indicated above, with aldehyde of the formula (VII), wherein $R_8$ represents an alkyl radical of one to ten carbon atoms, or a phenyl, or a substituted phenyl, in the present of an organic solvent, to give a compound of imine of the formula (VI), wherein $R_1$ and $R_8$ have the meanings as indicated above;

(c) formation of imine of the formula (VIII), wherein $R_1$, $R_2$, $R_3$ and $R_8$ have the meanings as indicated above, with selective condensation of α, β-unsaturated acid derivatives of formula (II), wherein $R_2$ and $R_3$ have the meanings as indicated above, and $R_5$ represents a halogen atom or $OR_9$, wherein $R_9$ represents an alkyl radical of one to six carbon atoms; and $R_6$ represents an alkyl radical of one to six carbon atoms, and imine of formula (VI), wherein $R_1$ and $R_8$ have the meanings as indicated above, in the present of a base and a polymer inhibitor in an organic solvent at reflux temperature; and (d) formation of triazolopyrimidine derivatives of formula (I) from the compound of the formula (VIII), wherein $R_1$, $R_2$, $R_3$ and $R_8$ have the meanings as indicated above, in the present of an acid at room temperature to refluxing temperature.

2. A process according to claim 1, wherein the alkyl amine of the formula (IV) is added slowly into the mixture of the dialkyl cyanodithioimino carbonate of the formula (V) at room temperature and then add hydrazine dropwisely after heating to reflux, to give a compound of diamino-1,2,4-triazole of the formula (III), in the step (a).

3. A process according to claim 1, wherein the alkyl amine is used 1 to 2 equivalent.

4. A process according to claim 1, wherein the dialkyl cyanodithioimino is used 1 equivalent.

5. A process according to claim 1, wherein the solvent in the step (a) can use water, acetonitrile or alcoholic solvent.

6. A process according to claim 5, wherein the alcoholic solvent can be methanol, ethanol, propanol or butanol.

7. A process according to claim 1, wherein the hydrazine is used 1 to 4 equivalent.

8. A process according to claim 1, wherein 1 to 5 equivalent of aldehyde of the formula (VII). is reacted with 1 equivalent of the diamino-1,2,4-triazole of the formula (III) in an organic solvent at 50~150° C. in the step (b).

9. A process according to claim 1, wherein the step (b) can be occurred under acid catalysis.

10. A process according to claim 9, the acid catalyst can be organic or inorganic acid.

11. A process according to claim 10, the acid catalyst can be acetic acid, toluene sulfonic acid, sulfuric acid, or hydrogen acid.

12. A process according to claim 1, wherein the solvent in the step (b) can use acetonitrile, toluene, xylene, chlorobenzene, chloroform, dichloromethane, ethylene dichloride or alcoholic solvent.

13. A process according to claim 12, wherein the alcoholic solvent can be methanol, ethanol, propanol or butanol.

14. A process according to claim 1, wherein 1 to 2 equivalent of α, β-unsaturated acid derivatives of the formula (II) is reacted with 1 equivalent of the imine of the formula (VI) at 40~150° C. in the step (c).

15. A process according to claim 1, wherein the base in the step (c) is used 0.1 to 2 equivalent.

16. A process according to claim 1, wherein the polymer inhibitor in the step (c) is used 0.005 to 0.2 equivalent.

17. A process according to claim 1, wherein the solvent in the step (c) can use acetonitrile, toluene, xylene, chlorobenzene, chloroform, dichloromethane or ethylene dichloride.

18. A process according to claim 1, wherein the base in the step (c) can be metal carbonate or metal hydrogencarbonate.

19. A process according to claim 18, wherein the metal can be Li, Na, K, Rb, Cs, Be, Mg, Ca, Sr, or Ba.

20. A process according to claim 18, wherein the base is potassium carbonate.

21. A process according to claim 1, wherein the polymer inhibitor can use hydroquinone or nomomethyl ether hydroquinone.

22. A process according to claim 21, wherein the polymer inhibitor is p-methoxy phenol.

23. A process according to claim 1, wherein the acid in the step (d) can be inorganic or organic acid.

24. A process according to claim 23, wherein the acid can use hydrochloride, sulfuric acid, acetic acid or oxalic acid.

25. A process according to claim 1, wherein the solvent in the step (d) can use water, methanol, ethanol, acetonitrile, toluene, xylene, chlorobenzene, chloroform, dichloromethane or ethylene dichloride.

26. A process for preparation of triazolopyrinidine derivatives of the formula (I)

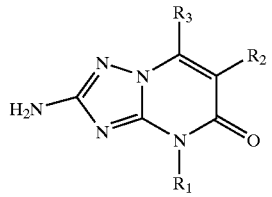

(I)

wherein $R_1$, $R_2$ and $R_3$ have the meanings as indicated above, comprises preparing rapidly diamino-1,2,4-triazole of the formula (III), wherein $R_1$ has the meaning as indicated above, from dialkyl cyanodithioimino-carbonate of the formula (V), wherein R has the meaning as indicated above;

protecting and deprotecting of amino group; and selective condensation of α, β-unsaturated acid derivatives of the formula (II), wherein $R_2$, $R_3$, $R_5$ and $R_6$ have the meanings as indicated above and imine of the formula (VI), wherein $R_1$ and $R_8$ have the meanings as indicated above.

* * * * *